(12) United States Patent  
Hamilton

(10) Patent No.: US 7,686,231 B2  
(45) Date of Patent: Mar. 30, 2010

(54) SECURE PRODUCT AUTHENTICATION METHOD AND SYSTEM

(75) Inventor: Robert S. Hamilton, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 493 days.

(21) Appl. No.: 11/140,448

(22) Filed: May 27, 2005

(65) Prior Publication Data

US 2006/0266827 A1 Nov. 30, 2006

(51) Int. Cl.  
*G06K 19/06* (2006.01)

(52) U.S. Cl. ........................ 235/494; 235/375

(58) Field of Classification Search ............... 235/383, 235/492, 494, 375; 33/383, 492, 494, 375  
See application file for complete search history.

(56) References Cited

U.S. PATENT DOCUMENTS 4,980,544 A * 12/1990 Winter ..................... 235/436
7,059,533 B2 * 6/2006 Van Rens .................. 235/492
7,172,117 B2 * 2/2007 Moore ....................... 235/385
7,287,691 B2 * 10/2007 Montanari ................. 235/380
2006/0255130 A1 * 11/2006 Whewell et al. ........... 235/383

* cited by examiner

*Primary Examiner*—Ahshik Kim  
(74) *Attorney, Agent, or Firm*—Fay Sharpe LLP

(57) ABSTRACT

A system for authenticating a secure product includes a an exposed first identification, an unexposed second identification, a database, and an interface. The exposed first identification and an unexposed second identification are adapted to affix to a secure product. The second identification corresponds to the first identification. The database stores the first identification and the second identification. The interface communicates with the database and is adapted to receive input of at least one of the first identification and the second identification, query the database in response to the input and receive an output of at least one of the first identification and the second identification from the database. A method for authenticating a product is also disclosed.

13 Claims, 5 Drawing Sheets

| Product Code | Public Unique ID | Authentication Mark | Verification Mark | Time Stamp | Time of Purchase |
|---|---|---|---|---|---|
| BRAND X MEDICATION | 12345 | !!#45ef | #$545IK | 12-Dec-04 | 12/12/2004 12:34 |
| BRAND X MEDICATION | 12346 | GH$$%FT | ^^$FGHY | 12-Dec-04 | |
| BRAND X MEDICATION | 12347 | HJ77%( | $%GHT78 | 12-Dec-04 | |

FIG. 5

SECURE PRODUCT AUTHENTICATION METHOD AND SYSTEM

BACKGROUND

High-value products rely on distinctive labels and/or packaging to provide confidence to a consumer that the product is authentic. These high-value products include medications, such as oral and intravenous medications, brand label liquor, brand label clothing items and accessories, as well as other expensive products. Counterfeiters can copy the distinctive labels and/or packaging so that a consumer thinks that he is purchasing an authentic product when that is not the case.

Manufacturers and other suppliers of these high value products use holographic images, or other indicia that is difficult to copy in their labels and/or packaging; however, counterfeiters can reuse the distinctive label and/or packaging with an unauthentic product. Furthermore, providers, such as unscrupulous retailers, can collude with counterfeiters to defraud consumers into thinking that they purchased an authentic product when that is not the case.

SUMMARY

A method for authenticating a secured product includes the following steps: affixing to a product an exposed first identification and an unexposed second identification that corresponds to the first identification; storing the first identification and the second identification in a database; revealing the second identification; supplying at least one of the first identification and the second identification to the database; and returning at least one of the first identification and the second identification from the database.

A system for authenticating a secure product includes an exposed first identification, an unexposed second identification, a database, and an interface. The exposed first identification and an unexposed second identification are adapted to affix to a secure product. The second identification corresponds to the first identification. The database stores the first identification and the second identification. The interface communicates with the database and is adapted to receive input of at least one of the first identification and the second identification, query the database in response to the input and receive an output of at least one of the first identification and the second identification from the database.

BRIEF DESCRIPTION OF THE FIGURES

FIG. 5 is an example of data stored in a database of the system of FIG. 1.

DETAILED DESCRIPTION

Figure 1:
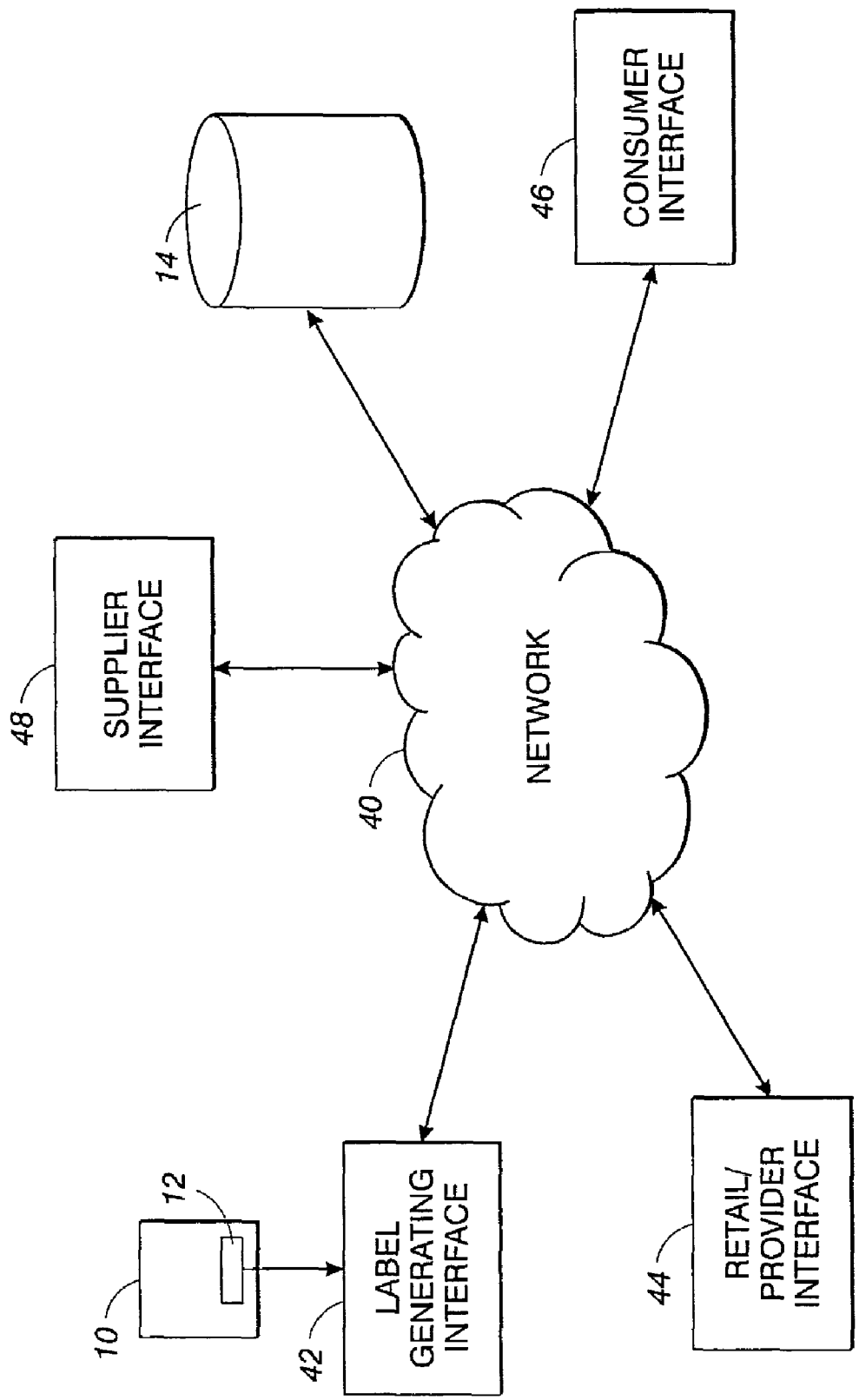
FIG. 1 is a schematic view of a system for authenticating a secure product.

With reference to FIG. 1, a system for authenticating a secure product 10 generally includes a label 12 and a database 14 for storing information about the product and the label. Queries can be made to the database 14 to determine the authenticity of the secure product 10.

Figure 2:
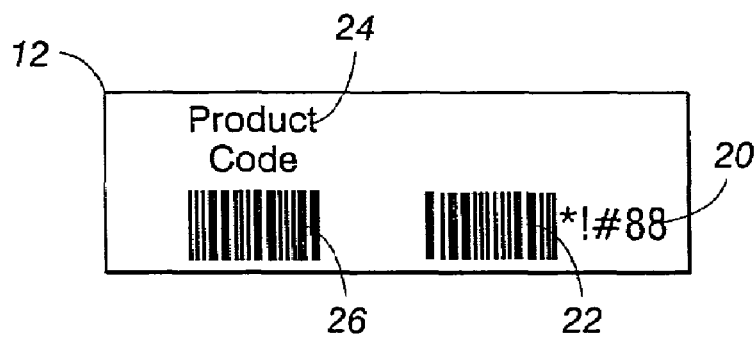
FIG. 2 is a plan view of a label for use with the system of FIG. 1 where authentication indicia are covered by an obfuscating material.

With reference to FIG. 2, the label 12 that is affixed to the secure product 10 in the depicted system includes an authentication mark 20, a verification code 22, a product code 24, and a public unique identification (ID) 26. The authentication mark 20 is read by the consumer at the point of sale, and thereafter. The verification code 22 can complete an electronic transaction, which will be described in more detail below. The public unique ID 26 is a code that is unique to each instance of the product 10. The product code 24 generally refers to the type of product, e.g. medication, liquor, clothing. In the embodiments depicted in FIGS. 2-4, the marks and/or codes 20-26 are shown on a single label 12, however the marks can be supplied on a plurality of different labels that are affixed to the secure product 10.

Figure 3:
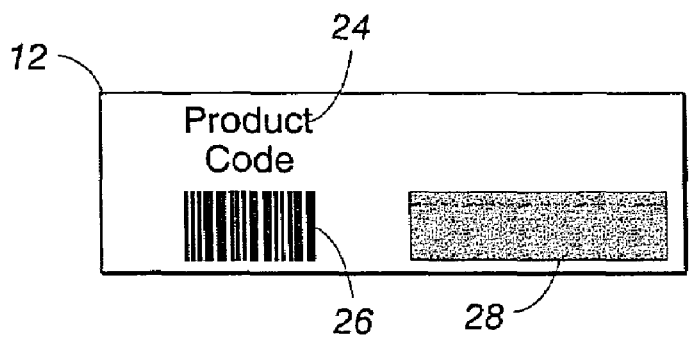
FIG. 3 is a plan view of the label of FIG. 2 where the obfuscating material has been removed from the label.

The authentication mark 20 can comprise any combination of letters, numbers, symbols, and the like that will serve to aid the consumer in verifying that when revealed, that the transaction is authentic. The verification code 22 can also comprise any combination of letters, numbers or symbols, as well as a machine readable code, such as a bar code, that serves to aid in verifying that when revealed, that the transaction is both authentic and completed. As seen in FIG. 3, an obfuscating material 28, such as a scratch-off material as found on known scratch-off instant lottery tickets, is laid over an area that encompasses both the authentication mark 20 and the verification code 22. Other obfuscating material can be used such as a tear-off cover and the like. To provide further tamper resistance, a complex graphic 30 can cover both the obfuscating material 28 and an area of the label 12 adjacent the obfuscating material. The complex graphic 30 can be applied so that if the obfuscating material 28 is removed, it is difficult to recreate the complex graphic to match up with the area of the label adjacent the obfuscating material.

Figure 4:
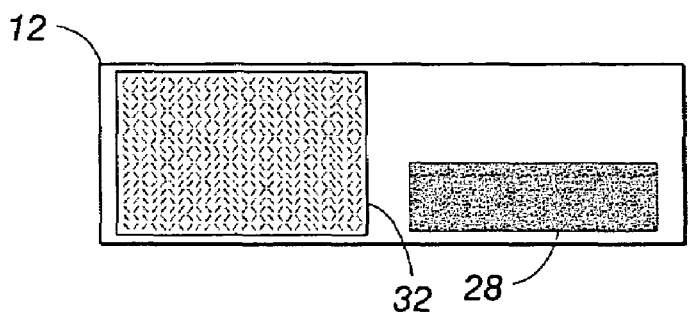
FIG. 4 is an alternative embodiment of a label for use with the system of FIG. 1.

The public unique ID 26 corresponds to the authentication mark 20 and the verification code 22 printed on the label 12 when the information is stored in the database 14. The public unique ID 26 can comprise any combination of letters, numbers or symbols, as well as a machine readable code, such as a bar code. Likewise, the product code can comprise any combination of letters, numbers or symbols, as well as a machine readable code, such as a bar code. As seen in FIG. 3, the product code 24 and the public unique ID 26 are visible on the label 12, i.e. not covered by the obfuscating material 28. With reference to FIG. 4, in an alternative embodiment an RF tag 32 can be affixed to the label and the information to which the product code 24 and the public unique ID 26 refer in the embodiment depicted in FIGS. 2 and 3 can be embedded in the RF tag 32. Such a configuration can further automate the shipping and verification procedures.

The database 14 can be stored on a computer and/or server, such as those known in the art. The server can be secure in that access to the server and/or the ability to change data on the server can be limited so that only certain individuals with access can change and/or access the information stored on the database. The database can include hardware and/or software that allows the database to be queried and to return information, as described below. The database 14 can be thought of as storing the product label information in a spreadsheet-type format, as shown in the example depicted in FIG. 5. FIG. 5 only depicts three rows of a spreadsheet 34; however, it is understood that the database can include much more information. Each row of information corresponds to a different label that corresponds to each instance of the product. In addition to storing label information, i.e. product code, public unique ID, verification code, and authentication mark, the database can also include the time at which the label was produced, for example in column 36, and transactional information, for example in column 38, which will be described in more detail below.

As seen in FIG. 5, the same product code 24, i.e. BRAND X MEDICATION, can correspond to different public unique IDs 26. For example in the database spreadsheet 34, the product codes 24a, 24b and 24c are the same for each label; each public unique ID 26a, 26b and 26c corresponds to a different respective authentication mark 20a, 20b and 20c and to a different respective verification code 22a, 22b and 22c.

The authentication system further includes a network 40 for allowing different entities to communicate with the database 14. The network 40 can be a local area network (LAN), a wide area network (WAN), or any other type of network such as an intranet, extranet, as well as the Internet. The network 40 can include a plurality of smaller networks that include private networks, public networks and secure public networks.

The authentication system further includes a label generating interface 42 that communicates with the database 14 via the network 40. The label generating interface 42 can include a computer that is connected to a modem where information is received by the computer and transferred to the database 14. Also, the interface 42 can connect directly to the database 14 via a port connection, e.g. parallel or serial port connection, that connects to a private network and/or a secure public network. The label generating interface 42 can also include label generating software that allows a manufacturer, or other authorized entity, to input requests to generate labels 12. The information for each label 12, i.e. the product code 24, the public unique ID 26, the corresponding authentication mark 20 and the corresponding verification code 22, can be input into the database 14 via the label generating interface 42.

The authentication system further includes a retailer/provider interface 44 that communicates with the database 14 via the network 40. The retailer/provider interface 44 provides the public unique ID 26 and the verification code 22 found on the label 12 to the database 14. The retailer/provider interface 44 can include a reader, such as a bar code reader, a computer, such as one found in a cash register, and the like. Other known devices and software that can receive input and connect to the network 40 are also contemplated, for example a web portal that can receive information from the retailer/provider. The retailer/provider interface 44 can also include a display and a processor to allow the retailer to display information received from the database and to run desired programs. The retailer/provider interface 44 is connected to the network 40 so that the database 14 can be queried, which will be described in more detail below.

The authentication system further includes a consumer interface 46 that communicates with the database 14 via the network 40. The consumer interface 46 includes any device that can connect to the network, including a mobile phone, a computer, a personal digital assistant, a web portal, as well as other known devices and software. The consumer interface 46 is also connected to the network 40 so that the database 14 can be queried, which will be described in more detail below.

The authentication system can further include a supplier interface 48. The supplier interface 48 can be a different interface than the label generating interface 42, even though the supplier is the one who interacts with both, in that the supplier interface can receive information from the database 14 about the transaction between the retailer/provider and the consumer. The same interface that was used to input the requests to generate the labels, i.e. the label generating interface 42 can also be the same interface that receives transaction data from the database.

Figure 6A:
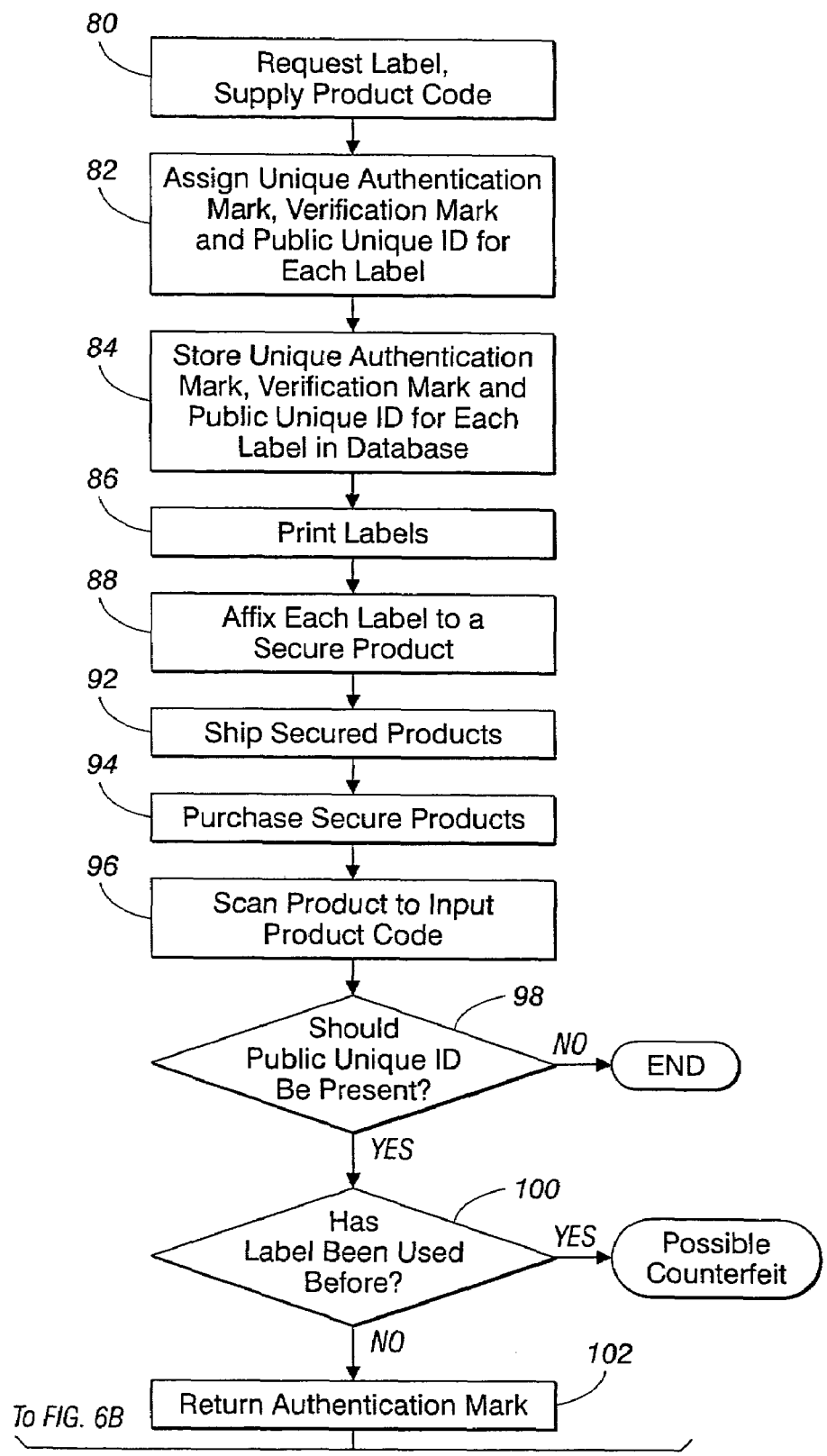
FIG. 6 is a flow diagram of a method for authenticating a secure product.
Figure 6B:
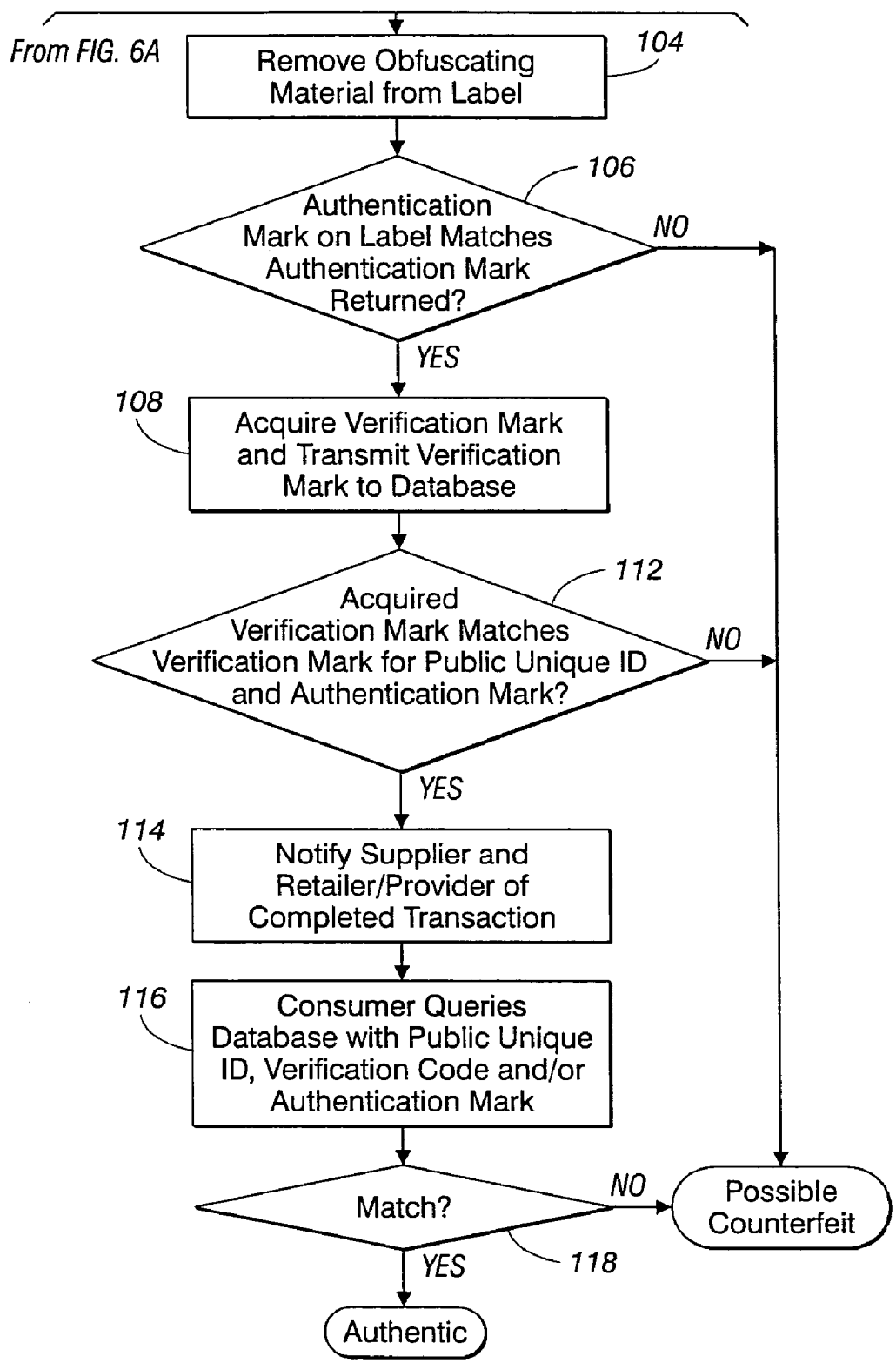

With reference to FIG. 6, a method for authenticating the secure product 10 will be described. At step 80, a supplier makes a request, via the label generating interface 42, for the label 12 by supplying a product code 24. The supplier will typically be the company or entity that is the source of the secure product 10. Also, the supplier can be a manufacturer who contracts with the company who maintains that it is the source of the product.

At step 82, label generating software, which can comprise a portion of the label generating interface 42, assigns a first unique identification and a second unique identification for each label 12 desired for the product code 24. The first identification can include the authentication mark 20 and the verification code 22 that is depicted in FIG. 2, and the second identification can include the public unique ID 26 that is also depicted in FIG. 2. The label generating software can also time stamp the time at which the first identification and the second identification was assigned to each label, which is shown at column 36 in FIG. 5.

At step 84, the first identification and the second identification for each label for the product code 24 are stored in a database 14 (FIG. 1). The information is received via the label generating interface 42 (FIG. 1). The information can be stored in a spreadsheet-type arrangement, as described above and shown in FIG. 5, where each public unique ID 26 corresponds to a unique authentication mark 20 and a unique verification code 22.

At step 86, a label 12 (FIGS. 2, 3 and 4) is manufactured that includes the product code 24, the corresponding first identification, e.g. the authentication mark 20 and the verification code 22, and the corresponding second identification, e.g. the public unique ID 26. At step 86, the label generating software formats print commands to produce a desired number of labels 12 (FIG. 1) each label containing art work, the product code 24, the public unique ID 26, the corresponding verification code 20, and the corresponding authentication mark 22. Also, at step 86, obfuscating material 28 is laid over an area that encompasses both the authentication mark 20 and the verification code 22. As mentioned above, a radio frequency identification tag 34 (FIG. 4) can be affixed to the label 12 and/or product 10 in lieu of the product code 24 and/or the public unique ID 26.

At step 88, the label 12 is affixed to the secure product 10 (FIG. 1). At step 92, the secure product 10 is shipped from the supplier to the retailer/provider, which can include at least one of the following: a retailers, providers and wholesalers. Tracking of the product through the product chain can be done through the public unique ID 26. Where the public unique ID is embedded in an RF tag 34 (FIG. 4), the tracking process can be further automated. Eventually, the secure product 10 is purchased, which is denoted at step 94.

At step 96, at the time of purchase by the consumer, the product 10 is scanned, e.g. using the retailer/provider interface 44, for the product code 24 and the public unique ID 26. At step 98, the database 14 is queried. If the product code 24 indicates that a public unique ID 26 should be present, then the public unique ID 26 is scanned and the retailer/provider interface 44 (FIG. 1) contacts the database 14 via the network 40. At step 100, the retailer/provider interface 44 queries the secured database 14 with the product code 24 and the public unique ID 26 to receive a status as to whether the label 12 has been previously used. If it is determined that the label 12 has been previously used it is an indication that the product 10 may be a counterfeit. If it is determined that the label 12 has not been previously used, then the database 14 returns to the retailer/provider interface 44 the corresponding second identification, which can include the authentication mark 20 and the verification code 22 at step 102. In the described method the authentication mark 20 is returned to the retailer/provider interface 44. After the database 14 returns the corresponding second identification, the database can indicate that the label used been used.

At step 104, the consumer removes the obfuscating material 28 from the label 12 revealing the authentication mark 20 and the verification code 22. At step 106, the consumer then verifies that the authentication mark 20 printed on the label 12 matches the authentication mark that has been returned to the retailer/provider interface 44. If the authentication mark 20 that has been uncovered by the consumer does not match the authentication mark delivered to the retailer/provider interface 44, then the product 10 may be a counterfeit. If the authentication mark 20 that has been uncovered by the consumer matches that on the retailer/provider interface 44, then, at step 108, the retailer/provider interface 44 acquires the corresponding verification code 22 and transmits the verification code 22 to the database 14 through the network 40.

At step 112, the database 16 determines whether the verification code 22 supplied by retailer/provider interface 44 matches the corresponding public unique ID 26 and the corresponding authentication mark 20. If the verification code 22 supplied by retailer/provider interface 44 does not match the verification code 22 for the corresponding public unique ID 26 and the corresponding authentication mark 20 then the product 10 may be a counterfeit. If the verification code 22 supplied by the retailer/provider interface 44 does match the verification code 22 for the corresponding public unique ID 26 and the corresponding authentication mark 20 then at step 114, the supplier, via the supplier interface 48 (FIG. 1) and the retailer via the retailer/provider interface 44 are notified of a completed transaction. At step 108, the network 40 can transfer the information of the completed transaction, e.g. the date and location, to a transaction log, which can be stored in the database 14 (FIG. 1). For example, the spreadsheet 34 depicted in FIG. 5 includes a column that includes the time of purchase for the secured products 10. In addition to the time of purchase and product label information, the transaction log can also include the location of the purchase, which can be transmitted via the retailer/provider interface 44, and other information, such as when queries were made to the database.

At step 116, when the transaction is complete in a normal fashion and if the consumer at a later time suspects collusion between the retailer and the supplier, then at step 116 the consumer, at a location other than the point of sale, can query the database, via the consumer interface 46, with the public unique ID 26, the verification code 22 and/or the authentication mark 20. At 118, the database 14 can return the product label information, such as the product code 24, the public unique ID 26, the verification code 22, and authentication mark 20 and the transactional information, e.g. time and location of sale, to the consumer. By allowing the consumer to check the information via a site other than the retailer/provider interface 44, for example via the supplier's website, the consumer can authenticate the product without the influence of the retailer.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A method for authenticating a product comprising:
   storing data in a database, the stored data including product identification data corresponding to an exposed product identification on a product that is to be authenticated and verification data corresponding to an unexposed verification identification on the product that is to be authenticated, wherein the verification data is associated with the product identification data;
   receiving, via an interface, product identification data based on the product identification on the product that is to be authenticated;
   querying the database with the received product identification data from the interface;
   returning a query result from the database based on the received product identification data, wherein the returned query result corresponds to the stored verification data associated with the received product identification data and is for determining the authenticity of the product by comparing the returned query result to the verification identification on the product after the verification identification has been exposed;
   storing transactional data in the database based upon a transaction between a retailer and a consumer involving the product, the transactional data including a date and/or location of the transaction and being associated with the product identification data;
   receiving, via an additional interface, further data based on at least one of the identifications on the product;
   further querying the database with the received further data from the additional interface; and
   returning a second query result from the database based on the received further data, wherein the returned second query result corresponds to the transactional data and is for determining the authenticity of the product by comparing the second query result to the date and/or location of the transaction.

2. The method of claim 1, wherein the product identification comprises an RF tag including identifying information.

3. The method of claim 1, wherein the product identification comprises a product code and a public unique ID.

4. The method of claim 1, wherein the verification identification comprises a verification code and an authentication mark.

5. The method of claim 4, wherein the authentication mark comprises at least one of the following: letters, numbers and symbols.

6. The method of claim 1, wherein the providing identifications comprises affixing a label to the product, the label comprising the product identification and the verification identification, wherein the verification identification is covered by an obfuscating material.

7. The method of claim 6, wherein the obfuscating material comprises a scratch-off material.

8. The method of claim 1, wherein the received data is based on the product identification on the product, wherein the query result is based on verification data associated with the received product identification data, and determining the authenticity comprises comparing the verification data from the query result to the verification identification on the product.

9. The method of claim 1, wherein the interface is located at a retail location and the additional interface includes at least one of a mobile phone, a computer, a personal digital assistant and a web portal.

10. The method of claim 1, wherein the verification identification comprises a verification code and an authentication mark.

11. A method for authenticating a product comprising:
providing identifications on a product that is to be authenticated, the identifications including a product identification, an authentication mark, and a verification code, wherein the authentication mark is covered with obfuscating material;
storing data in a database, the stored data including product identification data corresponding to the product identification, authentication data corresponding to the authentication mark and verification data corresponding to the verification identification, wherein the authentication data and the verification data are associated with the product identification data;
querying the database with data corresponding to the product identification on the product;
returning a query result from the database, wherein the query result corresponds to the authentication data that is associated with the product identification data corresponding to the product identification used to query the database for comparing the query result to the authentication mark on the product to determine the authenticity of the product;
querying again the database with the data corresponding to the product identification; and
returning a second query result from the database, wherein the second query result corresponds to the verification data that is associated with the verification code that is associated with the product identification data corresponding to the product identification used to query again the database for comparing the second query result to the verification code on the product to determine the authenticity of the product.

12. The method of claim 11, further comprising:
storing transactional data in the database based upon a transaction between a retailer and a consumer involving the product, the transactional data including a date and/or location of the transaction and being associated with the product identification data, the authentication data and the verification data;
querying again the database with at least one of the product identification, the authentication mark and the verification code; and
returning a third query result from the database, wherein the third query result corresponds to the date and/or location of the transaction for comparing the third query result to the date and/or location of the transaction to determine the authenticity of the product.

13. The method of claim 11, wherein the verification code is covered with the obfuscating material.

* * * * *